(12) United States Patent
Levy et al.

(10) Patent No.: US 8,665,441 B2
(45) Date of Patent: Mar. 4, 2014

(54) DENSITOMETER FOR MEASURING AN OPTICAL CHARACTERISTIC OF A FLUID

(75) Inventors: Nathan A. Levy, Ra'anana (IL); Ziv Gilan, Kfar-Harif (IL); Niv Shemtov, Rishon LeZion (IL)

(73) Assignee: Hewlett-Packard Indigo B.V., Maastricht (NL)

(*) Notice: Subject to any disclaimer, the term of this patent is extended or adjusted under 35 U.S.C. 154(b) by 36 days.

(21) Appl. No.: 13/410,716

(22) Filed: Mar. 2, 2012

(65) Prior Publication Data

US 2013/0229657 A1    Sep. 5, 2013

(51) Int. Cl.
*G01N 21/00*   (2006.01)
*G01N 21/85*   (2006.01)

(52) U.S. Cl.
CPC .................................. *G01N 21/8507* (2013.01)
USPC ........................................... 356/436; 356/432

(58) Field of Classification Search
CPC ............................ G01N 21/55; G01N 21/8507
USPC .................................................. 356/436–442
See application file for complete search history.

(56) References Cited

U.S. PATENT DOCUMENTS

| | | | | |
|---|---|---|---|---|
| 4,076,420 | A * | 2/1978 | De Maeyer et al. | 356/73 |
| 4,429,995 | A * | 2/1984 | Goulas | 356/343 |
| 5,567,294 | A * | 10/1996 | Dovichi et al. | 204/603 |
| 5,719,667 | A * | 2/1998 | Miers | 356/73 |
| 6,365,109 | B1 * | 4/2002 | Jeng et al. | 422/547 |
| 6,426,045 | B1 * | 7/2002 | Jeng et al. | 422/82.05 |
| 2002/0109844 | A1 * | 8/2002 | Christel et al. | 356/417 |
| 2003/0048432 | A1 * | 3/2003 | Jeng et al. | 356/39 |
| 2009/0268195 | A1 * | 10/2009 | Ilkov | 356/73 |
| 2010/0220326 | A1 * | 9/2010 | Frazier et al. | 356/419 |
| 2010/0290041 | A1 * | 11/2010 | Graham et al. | 356/246 |
| 2011/0141466 | A1 * | 6/2011 | Magnusson et al. | 356/319 |

* cited by examiner

*Primary Examiner* — Michael P Stafira (57) ABSTRACT

A device and method for measuring an optical characteristic of a fluid. The device, typically a densitometer includes a set of optical elements that include a light source, a collimating lens, a focusing lens, and a receiver, wherein a gap exists between the collimating lens and the focusing lens so as to allow the fluid to pass in between the lenses, and wherein at least one of the optical elements is tilted with respect to an optical axis.

20 Claims, 5 Drawing Sheets

DENSITOMETER FOR MEASURING AN OPTICAL CHARACTERISTIC OF A FLUID

BACKGROUND

Densitometers can measure the passage of light through a transparent or semitransparent material. The measured density of a measurable substance is typically determined by measuring attenuation in the intensity of light which reaches the optical detector of the densitometer after passing through the measurable substance, the measurement being related to the absorption of light of the measurable substance.

Most densitometers include a light source, often a laser, aimed at a photoelectric cell, arranged with a gap in between so as to allow placing the measurable substance in the gap. The electric current that is generated by the photovoltaic cell of the densitometer is typically directly proportional to the intensity of the incident light, and thus the optical density of the measurable substance is determined by comparing the generated current with a reference current value that corresponds to the passing of light from the light source to the photovoltaic cell when the gap is kept empty.

A multi-component device may be considered kinematically constrained when each of the degrees of freedom is fully constrained and typically, none are over-constrained.

Kinematic couplings or joints may typically refer to machined mechanical contacts. In some examples, the kinematic couplings may involve a kinematic tooth configured to be inserted into a kinematic slot.

Quasi-kinematic constraints typically allows for a small amount of over-constraint while providing high precision. Quasi-kinematic coupling typically includes contacts between corresponding machined mechanical contacts. In some examples, these contacts may be a cylinder on a flat surface or a ball in a cone. Typically, in contrast to kinematic coupling, by reducing the surface contact to a line, over-constraint may, in some examples, be reduced from three degrees of freedom to two degrees. Since line contacts typically only weakly over-constrain an interface between to mechanical contacts, more deterministic relationships may be able to be formed. These more deterministic relationships may provide improved repeatability in the construction of a mechanical unit or device.

BRIEF DESCRIPTION OF THE DRAWINGS

Examples are described in the following detailed description and illustrated in the accompanying drawings in which.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the methods and apparatus. However, it will be understood by those skilled in the art that the present methods and apparatus may be practiced without these specific details. In other instances, well-known methods, procedures, and components have not been described in detail so as not to obscure the present methods and apparatus.

Although the examples disclosed and discussed herein are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method examples described herein are not constrained to a particular order or sequence. Additionally, some of the described method examples or elements thereof can occur or be performed at the same point in time.

Unless specifically stated otherwise, as apparent from the following discussions, it is appreciated that throughout the specification, discussions utilizing terms such as "adding", "associating" "selecting," "evaluating," "processing," "computing," "calculating," "determining," "designating," "allocating" or the like, refer to the actions and/or processes of a computer, computer processor or computing system, or similar electronic computing device, that manipulate, execute and/or transform data represented as physical, such as electronic, quantities within the computing system's registers and/or memories into other data similarly represented as physical quantities within the computing system's memories, registers or other such information storage, transmission or display devices.

Figure 1:
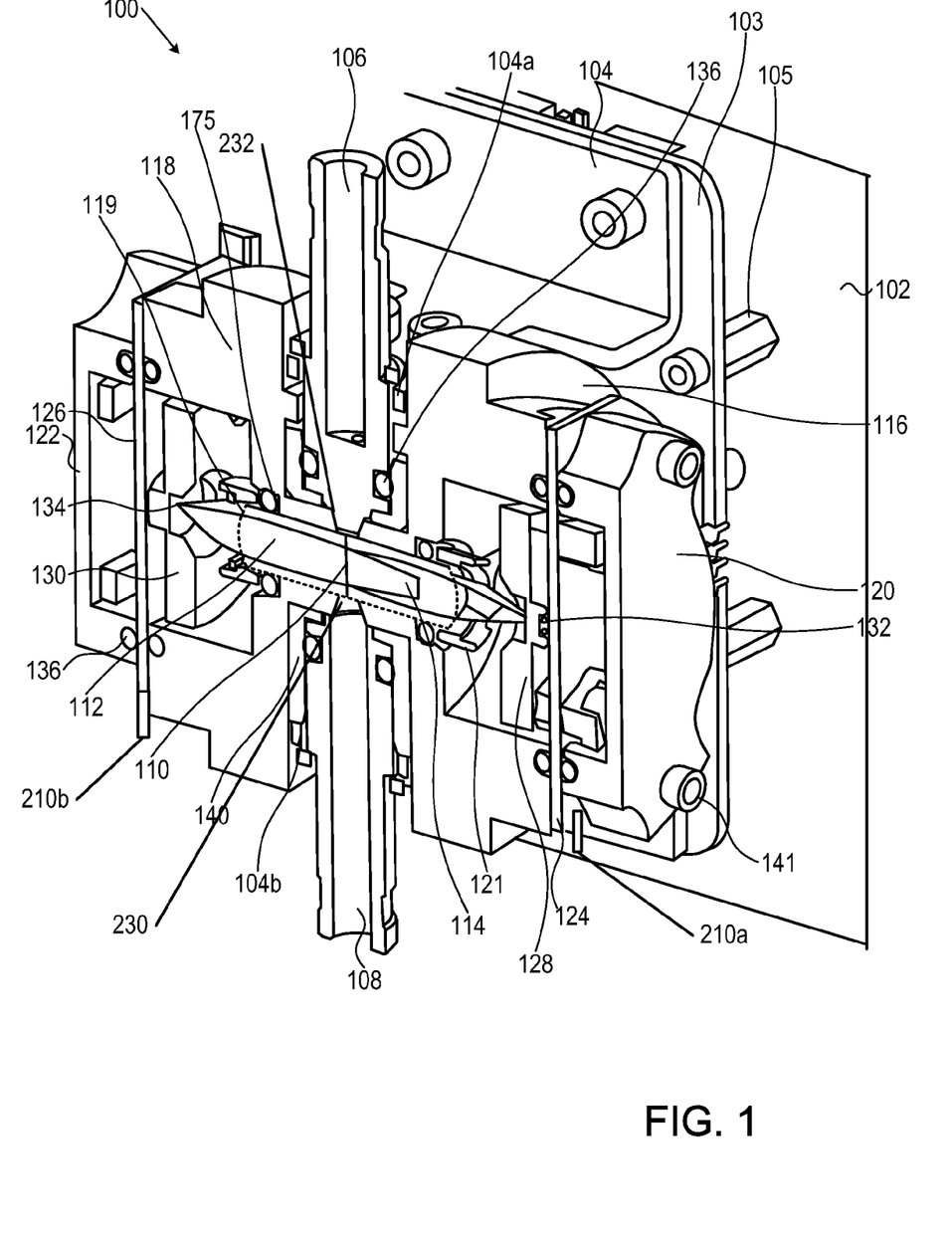
FIG. 1 is a schematic illustration of a horizontal, longitudinal cross-section according to an example.

FIG. 1 is a schematic illustration of a horizontal, longitudinal cross-section between a front and a back of a densitometer, along the long axis, and through frontal plane of the densitometer, the construction of the densitometer employing quasi-kinematic design elements.

An optical measuring device, typically a densitometer 100 may be manufactured as a multi-component measuring device. The device may typically be made up of at least two components, the components arranged consecutively, e.g., in a straight line.

The device typically has a high tolerance to within a few microns, typically +/−10 microns.

Elements of a densitometer may be constructed from materials, including aluminum. Other materials or combinations of materials, polymers and alloys, may be used. Densitometer 100 typically has a base plate 102, the base plate configured to support the separate components of the device. In some examples, base plate 102 may be a component of housing for densitometer 100.

In some examples, densitometer 100 may be configured to determine the percentage of solids in a fluid. In some examples, densitometer 100 may be configured to determine the amount of solid particles within a fluid In some examples densitometer may be configured to determine the percentage of non-volatile substances (% NVS) in the fluid, such as, for example, % NVS, where the NVS are pigments of a colorant of ink for a printer via measuring light absorbance of the ink as it passes through densitometer 100.

Base plate 102 may include numerous niches, grooves, and/or additional structures for use in the construction of device 100, or in the integration of device 100 in a larger device. In some examples, this larger device may be a printer.

In some examples, densitometer 100 may be waterproof, or watertight. In some examples, densitometer 100 may be configured to be immersed, or partially immersed, in a liquid, e.g., ink. In some examples, densitometer 100 may be configured to be part of a larger assembly, e.g., a pathway for ink from an ink reservoir to a printer head.

A support plate 103 is typically coupled to base plate 102. In some examples, support plate 103 may be coupled to base plate 102 via a support column 105. In some examples, there may be one or a plurality of support columns 105 coupling support plate 103 to base plate 102. In some examples, spacer support columns 105 may be configured to provide a predetermined space between base plate 102 and support plate 103. In some examples, spacer support columns 105 may be configured to couple support plate 103 to base plate 102 without necessarily adding space between support plate 103 and base plate 102. In some examples, spacer support columns may be configured to house screws to couple separate components of densitometer 100.

In some examples, support plate 103 may be a component of the housing for densitometer 100.

Support structures 104a and 104b may be typically coupled to support plate 103. Support structure 104a typically may be coupled to an upper portion of densitometer 100, near an inlet 106. Support structure 104b may be coupled to a lower portion of densitometer 100, near an outlet 108.

Typically, inlet 106 may provide for a passage of a fluid from outside densitometer 100, in some examples, from an ink reservoir. In some examples, inlet 106 may provide for a passage of fluid through gap 110 within densitometer 100, and out densitometer 100 via outlet 108. Outlet 108 may lead to a printer head.

In some examples, once fluid has passed through a gap 110, the gap may be rinsed, the rinsing solution passing into gap 110 via rinse channels, including an upper rinse channel 232 and a lower rinse channel 230.

Gap 110 may be configured to provide travel of a fluid past focusing lens 112 and collimating lens 114. In some examples focusing lens 112 and collimating lens 114 are mirror images of each other. In some examples, focusing lens 112 and collimating lens 114 are rod lenses. Typically, the rod lenses will feature a polished spherical surface, ground circumferences and a polished base. In some examples, focusing lens 112 and collimating lens 114 may have anti-reflective coatings on their base, e.g., the non-curved, surfaces. In some examples, focusing lens 112 and collimating lens 114 may have anti-reflective coatings in other areas of the lenses.

In some examples, the shape of the rod lens may allow for a watertight sealing of an area around gap 110 by o-rings, the o-rings described below. Typically, the shape of a rod lens will allow for the watertight sealing of the area around gap 110 at a peripheral location of lenses 112 and 114 and not at the polished surface.

Gap 110 may, in some examples, may have a width. Typically the width may be between 250 and 400 microns wide, e.g., 300 microns wide.

Typically, focusing lens 112 and collimating lens 114 may be configured to focus a signal, e.g., light from a light source 132, e.g., a laser or an emitter, or other light sources, through gap 110. The emitted light may be collimated via collimating lens 114, prior to the light being detected by a receiver 134, e.g., a photodiode or other sensor or detector. In some examples, lens 112 and 114 may be rod lenses.

In some examples, densitometer may have a measuring set-up for measuring at least one optical characteristic of a fluid passing through gap 110. Typically measuring set-up may include optical sight source 132, lens 112, lens 114 and receiver 134. Typically, the optical characteristic being measured may include the optical density of the fluid.

Gap 110 is typically positioned at the intersection between the light from light source 132—the light typically travelling on an optical pathway through lens 112, gap 110, lens 114 and a receiver 134, and the flow of fluid from inlet 106 through gap 110 and through outlet 108.

In some examples, the flow of fluid may be perpendicular to the optical pathway. In some examples, the flow of fluid may be nearly perpendicular to the optical pathway. In some examples, the flow of fluid bisects gap 110 through the middle of gap 110. In some examples, the flow of fluid might not bisect gap 110 through the middle of gap 110.

In some examples, light source 132 may include a laser with a power of between 65 mw to 85 mW, e.g., 70 mW. For example, light source may include a 780 nm 70 mW laser. Other lasers may also be used.

In some examples, densitometer 100 may be configured to measure a dynamic range of signals, e.g., light from a laser, typically a range of 90 decibel milliwatts (dBm).

Typically, the signals may include measurable and/or determinable characteristics and/or properties. These include the frequency of the signal, the shape of signal and the amplitude of signal. In some examples, the signal may be describable as a wave function. In some examples, the signal may be describable as a sinusoid, i.e., a mathematical function describing a smooth, and in some examples, repetitive oscillation. Other characteristics and/or properties of signals may also be measurable and/or determinable.

In some examples, light source 132 may be able to generate a signal that may be locked-in with relation to some properties of the signal, the locked-in the properties of said signal may be communicated to processor, the processor residing on an electronic device, as described below. In some examples the locked-in signal may be described as a closed loop between light source 132 and coupled electronics, and receiver 134 and coupled electronics.

In some examples, lenses 112 and 114 may be supported in their position via at least two side pieces 116 and 118, where side piece 116 is typically on the right side of gap 110 and side piece 118 is on the left side gap 110. In some examples, focusing lens 112 may be supported by a lens holder 119. In some examples, collimating lens 114 may be supported by lens holder 121, as described below.

In some examples side piece 116 and side piece 118 may have the same structural design with the coupling of the two side pieces configured to have rotational symmetry, e.g., side piece 116 is coupled to a spacer piece 140, spacer piece 140 may be a block, and side piece 118 may be flipped 180 degrees and coupled to another side of spacer piece 140. In some examples, spacer piece 140 may have two sides. In some examples, the two sides of spacer piece 140 may have rotational symmetry, i.e., a first side is a 180 degree rotation of a second side. In particular the two sides of spacer piece 140 configured to be coupled to side pieces 116 and 118 may be symmetrical in all aspects except for the steps, the steps described below, wherein the steps have a rotational symmetry.

A cap 120, or other component configured to cover light source 132, may be typically screwed onto side piece 116 via one or a plurality of screws 141. In some examples, other methods of coupling components together may also be used.

A cap 122, or other component configured to cover receiver 134 may be typically screwed onto side piece 118 via one or a plurality of screws 141. In some examples, other methods of coupling components together may also be used.

In some examples, electronic device 124, typically an integrated circuit, printed circuit board (PCB), printed wiring board (PWB), etched wiring board, printed circuit assembly (PCA), printed circuit board assembly (PCB Assembly or PCBA) may be used to mechanically support and electrically connect electronic components using conductive pathways, tracks or signal traces etched from copper sheets laminated onto a non-conductive substrate within densitometer 100. Typically, electronic device 124 may be coupled to light source 132. In some examples, light source 132 may be physically coupled to electronic device 132.

Light source 132 may send a signal, typically light, through lens 114 through gap 110, any fluid in gap 110, lens 112 to receiver 134.

Electronic device 124 may be configured to interface with a control unit, described below. Electronic device 124 may be configured to be in contact, either wired or wirelessly, with an electronic device coupled to receiver 134.

Electronic device 124 may have electronic connectors; the electronic connects configured to couple electronic device 124 to other components within densitometer 100. In some examples, the electronic contacts may be configured to couple electronic device 124 to other components or devices outside of densitometer 100. Typically, electronic device 124 may be connected to connections to other components in densitometer 100, or components outside densitometer 100 via electronic connectors 210a.

In some examples, electronic device 124 may be configured to be in communication with light source 132. In some examples, electronic device 124 may be configured to control light source 132, such that light source 132 produces a signal, typically light, with predefined characteristics.

In some examples, predefined characteristics may include a known wave function or know wave shape with know frequency and amplitude. In some examples, electronic device 124 may be configured to control light source 132 such that light source 132 produces a signal definable as a sine wave with a predefined frequency of one kilohertz.

Typically electronic device 124 may be in communication with receiver 134. In some examples, electronic device 124 may receive a detected signal from receiver 134. Typically, electronic device 124 may determine the concentration of a fluid by analyzing the detected signal from receiver 134 and comparing detected signal with the generated signal from light source 132.

In some examples, electronic device 124 may be configured to determine the predefined wave of a signal to be a known wave function. Typically, electronic device 124 may be configured to determine the predefined wave of the signal to be a sine wave.

Typically, electronic device 124 may be in communication with receiver 134 such that receiver 134 is configured to specifically filter out a signal not definable by the sine wave with the known frequency produced by light source 132 from other noise in densitometer 100.

In some examples, electronic device 124 may be in communication with receiver 134 such that receiver 134 is configured to specifically filter out a signal not definable by a sine wave with a frequency of one kilohertz, wherein light source 132 produces a signal describable as a sine wave with a frequency of one kilohertz.

In some examples, electronic device 124 may be in communication with receiver 134, such that receiver 134 is configured to detect a signal with a particular sine wave with know frequency and, in some examples, detect changes in amplitude of the signal.

In some examples, electronic device 124 may optimize and/or modulate the frequency of signal from light source 132, such that a ratio of signal to noise is changed.

Receiver 134 may be coupled to electronic device 126. In some examples, receiver 134 may be physically coupled to electronic device 126.

Electronic device 126 may typically be an integrated circuit, printed circuit board (PCB), printed wiring board (PWB), etched wiring board, printed circuit assembly (PCA), printed circuit board assembly (PCB Assembly or PCBA) may be is used to mechanically support and electrically connect electronic components using conductive pathways, tracks or signal traces etched from copper sheets laminated onto a non-conductive substrate within densitometer 100.

Electronic device 126 may have electronic connectors; the electronic connectors 210b configured to couple electronic device 126 to other components within densitometer 100. In some examples, the electronic contacts may be configured to couple electronic device 126 to other components or devices outside of densitometer 100. Typically, electronic device 124 may be connected to connections to other components in densitometer 100, or components outside densitometer 100 via electronic connectors 210b.

In some examples, there may be kinematic coupling between electronic device 124 and a light source holder 128. In some examples, there may be kinematic coupling between electronic device 124 and side piece 116.

In some examples, there may be kinematic coupling between electronic device 126 and a receiver holder 130. In some examples, there may be kinematic coupling between electronic device 126 and side piece 118.

Typically, kinematic coupling may involve a kinematic tooth, as described below on one component, in some examples, the one component may be side piece 116 and/or side piece 118. The kinematic tooth may be inserted into a kinematic slot, as described below in a second component. In some examples, the second component may be electronic device 124 or electronic device 126, or other components of densitometer 100. In some examples, kinematic slot may be in electronic device 124 and/or electronic device 126.

In some examples electronic device 124 and electronic device 126 may be mechanically identical or nearly identical while remaining electronically distinct.

In some examples, there may be one or a plurality of waterproofing connections 136, e.g., gaskets, o-rings, or other connectors, configured to waterproof densitometer 100, such that densitometer may be immersed fully or partially in a liquid, e.g., ink.

In some examples densitometer 100 may have gaskets 137, gaskets 137 configured to minimize or prevent fluid from leaking out of densitometer 100.

Typically, densitometer includes a spacer piece 140. In some examples, spacer piece may be shaped like a capital "I". Spacer piece 140 may be coupled via kinematic coupling to side piece 116 and side piece 118. Typically, kinematic coupling may involve a kinematic tooth, as described below, on one component, in some examples, on side piece 116 and/or side piece 118, inserted into a kinematic slot in a second component. In some examples, kinematic slot may be in spacer piece 140. In some examples, kinematic slot may be in another component within densitometer 100.

Typically, kinematic or quasi-kinematic coupling slots and teeth, described above and below, may fix some or all 6 degrees of freedom. Typically, these degrees of freedom include three translational degrees of freedom: x, y and z and three rotation, and yaw, pitch and roll. Typically, the 6 degrees of freedom may be fixed along the mating planes of the components, the mating planes as described below, coupled via kinematic coupling in densitometer 100.

Figure 2:
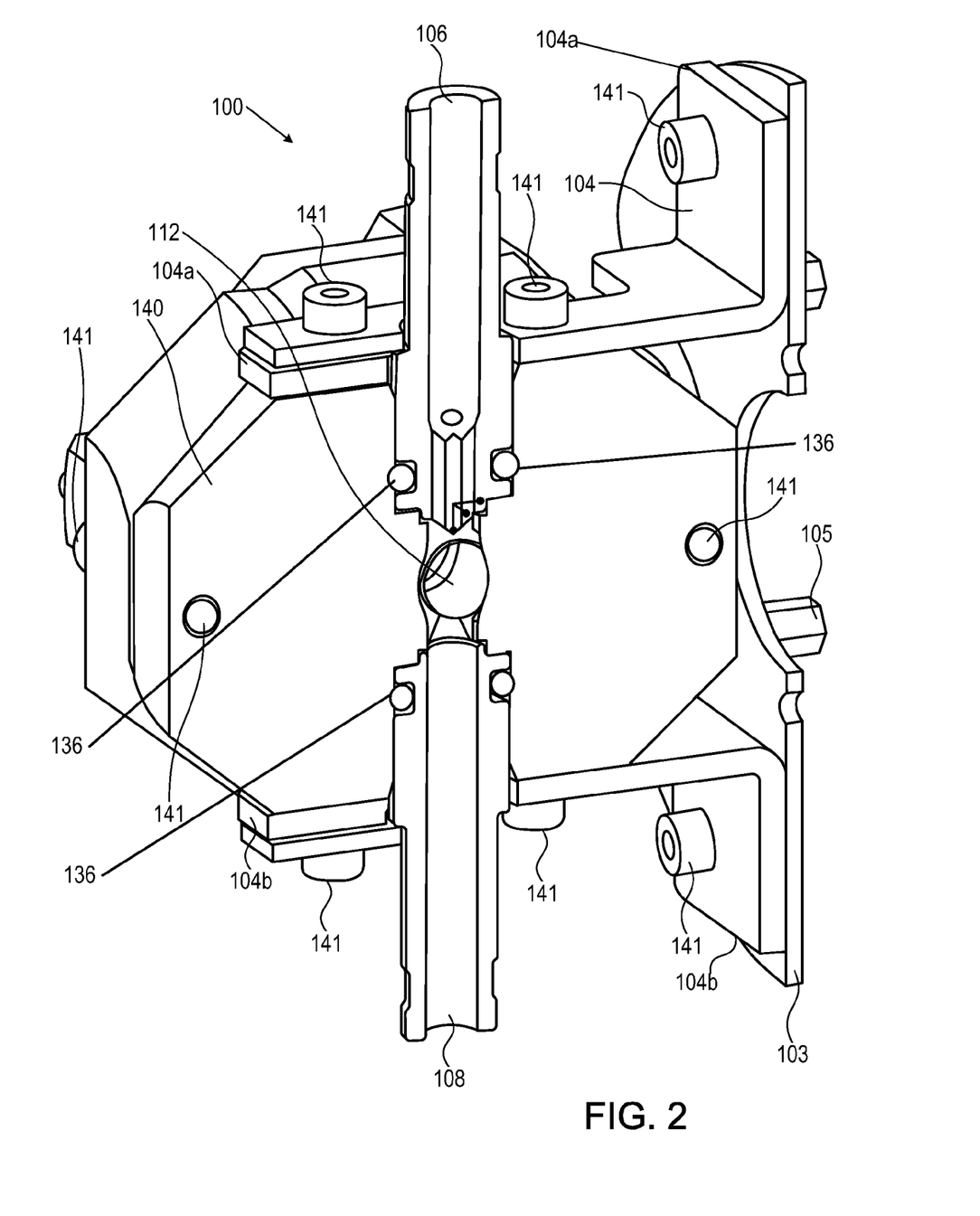
FIG. 2 is a schematic diagram of cross section along a lateral plane of a densitometer, according to an example.

FIG. 2 is a schematic diagram of cross section between along a lateral plane of a densitometer, between a left side and a right side of a densitometer and through the center line of the densitometer, with some of a spacer piece, and a side piece, cut away.

Typically, densitometer 100 components may be coupled together at one or a plurality of connection points, typically, via one or a plurality of screws 141, the screws typically fitting into screw sockets. In some examples, other methods of coupling components together may also be used.

The cross section depicted in the figure provides a view of the spacer piece 140 surrounding inlet 106, outlet 108 and gap 110, between lens 112 and lens 114. Parts of lens 112 may not be shown in this illustration.

As described above, support plate 103 is coupled a base plate via spacer support columns 105. In some examples, other methods of coupling support plate 103 to a base plate may also be used.

As described above, support structure 104 may be typically coupled to support plate 103. Support structure 104a typically may be coupled to an upper portion of densitometer 100, near an inlet 106. Typically, this coupling may be via screws 141. In some examples, other methods of coupling components together may also be used.

Support structure 104b may be coupled to a lower portion of densitometer 100, near an outlet 108. Typically, this coupling may be via screws 141. In some examples, other methods of coupling components together may also be used.

As described above, in some examples, there may be one or a plurality of waterproofing connections 136, e.g., gaskets, o-rings, or other connectors, configured to waterproof densitometer 100, such that densitometer may be immersed fully or partially in a liquid, e.g., ink, as described above.

Typically, spacer piece 140 is constructed and/or machined from a solid piece of material. In some examples, the material is steel. In some examples, the material may be an alloy. In some examples, other materials may be used.

Figure 3:
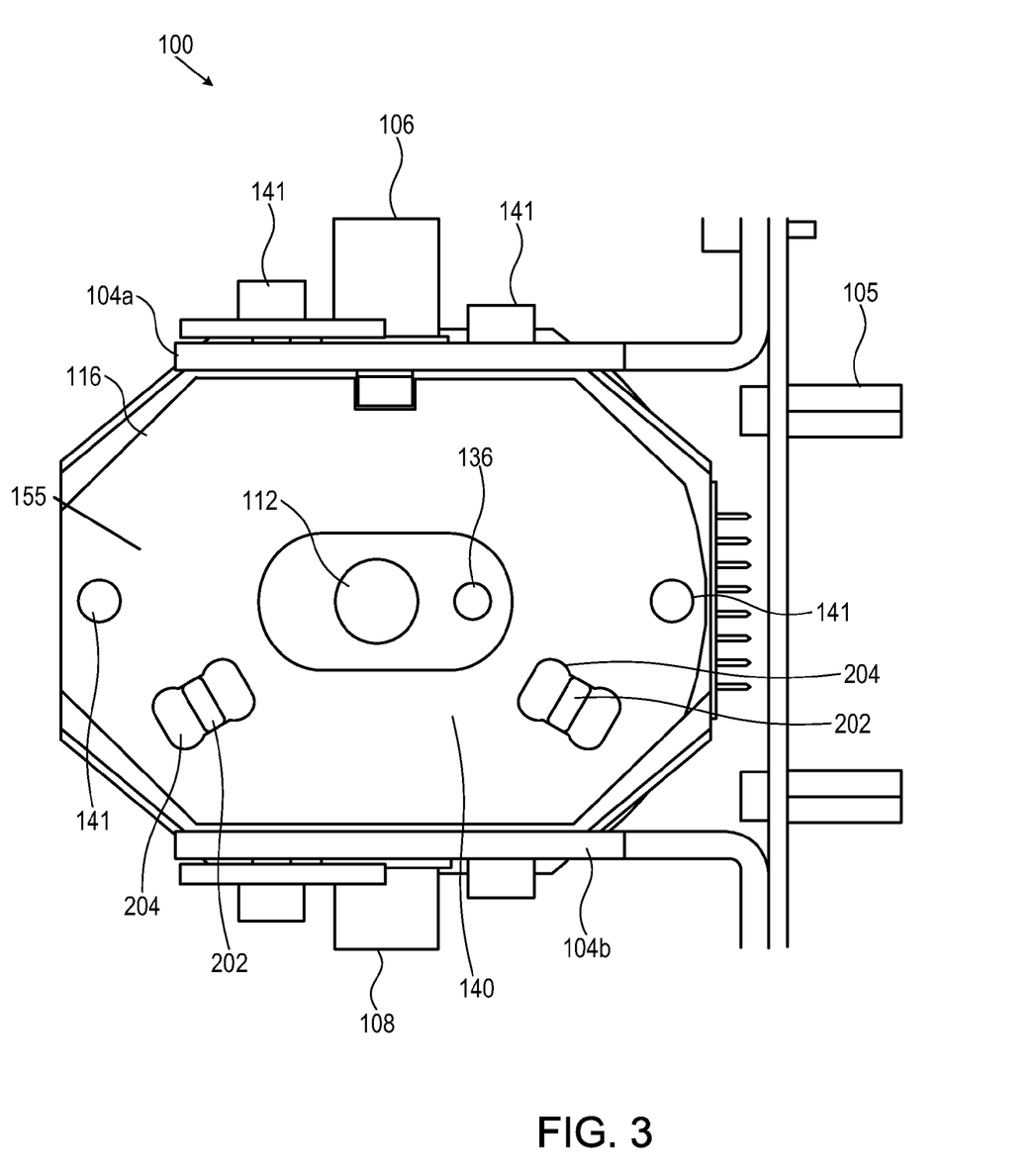
FIG. 3 is a schematic diagram of close-up of an off-center cross section, along a lateral plane of a densitometer, according to an example.

FIG. 3 is a schematic diagram of close up of an off-center cross section along a lateral plane of a densitometer, between a left side and a right side of a densitometer. The illustration depicts a mating plane where a spacer piece and a side piece are coupled.

As described above, typically, densitometer 100 components may be coupled together at one or a plurality of connection points, typically, via one or a plurality of screws 141. In some examples, other methods of coupling components together may also be used.

As described above support plate 103 is coupled a base plate via spacer support columns 105. In some examples, other methods of coupling support plate 103 to a base plate may also be used.

As described above, support structure 104 may be typically coupled to support plate 103. Support structure 104a typically may be coupled to an upper portion of densitometer 100, near an inlet 106. Typically, this coupling may be via screws 141. In some examples, other methods of coupling components together may also be used.

Support structure 104b may be coupled to a lower portion of densitometer 100, near an outlet 108. Typically, this coupling may be via screws 141. In some examples, other methods of coupling components together may also be used.

Typically, this coupling may be via screws 141. In some examples, other methods of coupling components together may also be used.

As described elsewhere, in some examples, there may be one or a plurality of waterproofing connections 136, e.g., gaskets, o-rings, or other connectors, configured to waterproof densitometer 100, such that densitometer may be immersed fully or partially in a liquid, e.g., ink, as described above.

The cross section depicted in the figure provides a view of the spacer piece 140 surrounding inlet 106, outlet 108 and gap 110, between lens 112 and lens 114. Parts of lens 112 may not be shown in this illustration, as described above.

Components of densitometer 100 are further coupled together via kinematic or quasi kinematic coupling.

Typically, one component of densitometer 100 may have a slot 204, the slot configured to fix one or a plurality of degrees of freedom along a mating planes of two or more components, one mating plane 155 is show here illustratively, the illustrative mating plane combining both the slot 204 and the tooth 202 from the mating planes: The figure shows at least three teeth 202 illustratively. Typically, teeth 202 are part of side pieces 116 and 118 and mate with slots 204. Typically, spacer piece 140 may have slots 204 that mate with teeth 202 on side pieces 116 and 118. In some examples, spacer piece may have teeth 202 that mate with slots 204 on side pieces 116 and on side piece 118.

Typically, slot 204 may be configured to fix one or a plurality of degrees of freedom along mating planes of two or more components via engaging a tooth 202. Typically, in quasi kinematic coupling, tooth 202 may be short and/or straight. In some examples, tooth 202 may have a very small clearance with slot 204. Typically, this smaller clearance may replace point contact, and in some examples, may enable the use of a softer material in the surfaces of densitometer 100 in general, and at the points of contacts, in particular.

In some examples, slots 204 may have precise dimensions in one axis, e.g., longitudinally, and may have relief dimensions in a second axis, e.g., laterally.

In some examples, slots 204 may have relief dimensions in one axis, e.g., longitudinally, and may have precise dimensions in a second axis, e.g., laterally.

In some examples, some components of densitometer 100 may have slots 204 for coupling to side pieces 118 and 116 and may also have slots 204 for coupling to other and/or additional components of densitometer 100.

In some examples, electronic device 124 of densitometer 100 may have slots 204 for coupling to side piece 116 and may also have slots 204 for coupling to light source 132.

In some examples, some slots 204 in electronic device 124, may be configured for coupling to side piece 116, and may form the geometry of a larger triangle. In some examples, some slots 204 in electronic device 124, may be configured for coupling to light source 132, and may form the geometry of a smaller triangle.

In some examples, electronic device 126 of densitometer 100 may have slots 204 for coupling to side piece 118 and may also have slots 204 for coupling to receiver 134.

In some examples, some slots 204 in electronic device 126, may be configured for coupling to side piece 118, and may form the geometry of a larger triangle. In some examples, some slots 204 in electronic device 126, may be configured for coupling to receiver 134, and may form the geometry of a smaller triangle.

Typically, spacer piece 140 may have one or a plurality of slots on a mating plane 155, the slots typically located in positions wherein they provide a triangular shape, the triangular shape creating a coupling centroid within a coupling triangle, in some examples, deterministically constraining some, in some examples, some or all six degrees of freedom of motion.

Typically, this triangular geometry provides a particular set of contact forces, contact stresses, and contact deflections. The coupling geometry may also typically provide improved precision with reasonable stiffness. The coupling geometry may also provide a weakly over-constrained interaction between the components, but allowing for sub-micron repeatability, a sealing contact, and high stiffness.

Typically, the coupling triangle geometry of this figure may be defined by lines which connect the coupling joints (e.g., tooth 202 and slot 204) coordinate systems. The coupling centroid may be defined as the intersection of the angle bisectors of the included angles of the coupling triangle.

Typically, the quasi kinematic coupling shown in the figure with the triangle geometry provides for easy assembly: if the coupling joints do not form an equilateral triangle, the coupling may typically be limited to be assembled in one configuration.

Typically, in a kinematic or quasi-kinematic coupling, the particular choice of coupling joint location has a strong influence on the rotational stiffness of the coupling. Typically, the device may be constructed such that the coupling joints are located to define the widest possible triangle, subject to geometry/size constraints of the design.

In some examples, stability and good overall stiffness may be achieved if slots 204 are oriented such that the normals to the planes containing the contact forces bisect the angles of the coupling triangle.

In some examples, coupling joints may be aligned to provide maximum resistance to error causing loads in one direction, while providing reasonable stiffness in the perpendicular direction.

Figure 4:
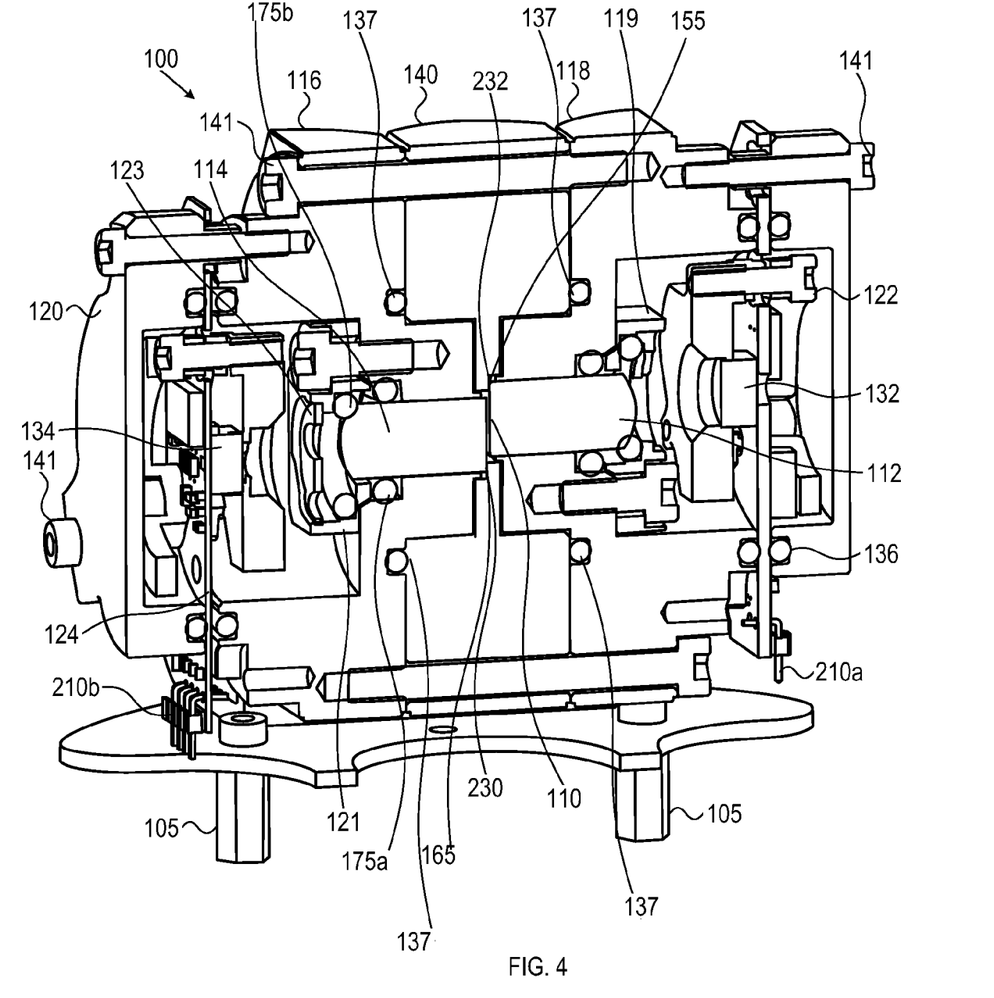
FIG. 4 is a schematic diagram of longitudinal cross-section of a densitometer between the front and back of the densitometer; and, FIG. 5 is a schematic illustration depicting some connections with a control unit.

Typically, to provide resistance to motion due to the friction induced torques between the screws 141, support plate 103, and base plate 102, the coupling joints are positioned such that they form as large a triangle as possible. FIG. 4 is a schematic illustration of a horizontal, longitudinal cross-section between a front and a back of a densitometer, along the long axis, frontal plane of the densitometer, and the construction of the densitometer employing quasi-kinematic design elements. Typically, densitometer 100 may have a gap 110 for a fluid to pass through in between lenses 112 and 114. In some examples, once fluid has passed through gap 110, the gap may be rinsed, the rinsing solution passing into gap 110 via rinse channels, including an upper rinse channel 232 and a lower rinse channel 230.

Typically, rinse channels may be configured to prevent too much fluid from passing in gap 110. In some examples, rinse channels are configured to divert some of the flow of fluid from inlet 106 around an edge of the gap toward outlet 108. In some examples, rinse channels may be configured to divert some of the flow of fluid from inlet 106 around at least two edges of the gap toward outlet 108. In some examples upper rinse channel may include at least two or a plurality of rinse channels. In some examples, lower rinse channel 230 may include two or a plurality of rinse channels. In some examples a flow of a liquid may be diverted by rinse channel 232 such that 50% of the fluid flowing from inlet 106 to outlet 108 passes through rinse channels 230 and 232. In some examples the fluid may be flowing through inlet 106 to outlet 108 at between 5 and 12 meters per second, e.g., 8 meters per second.

In some examples the diameter of collimating lens 114 and focusing lens 112 is less than the area of a set of steps supporting collimating lens 114 and focusing lens 112, the steps described below. Typically the difference in diameter between the set of steps and collimating lens 114 and focusing lens 112 provides an area for upper rinse channel 232 and a lower rinse channel 230.

In some examples the rinse channels may provide an area for fluid to pass through, the area between 0.4 and 1.0 millimeter $(mm)^2$, e.g., 0.7 $mm^2$. In some examples gap 110 may have dimensions of 0.3 mm by 7.0 mm In some examples the area of gap 110 and a set of 4 rinse channels, the 4 rinse channels including two upper rinse channels 232 and two lower rinse channels 230 may be equal or nearly equal in size.

Typically, as a signal, in some examples, light from light source 132 passes through focusing lens 112 toward gap 110, lens 112 may be held in position in densitometer 100 via a lens holder 119. Light typically then passes through gap 110, through collimating lens 114 toward receiver 134, wherein lens 114 is held in position via lens holder 121.

In some examples, light source 132 is coupled to electronic device 124, as described above. Electronic device 124 may be coupled to other components of densitometer 100 via kinematic or quasi kinematic coupling as described above. Typically, electronic device 124 may have electronic connections to other components in densitometer 100, or components outside densitometer 100. Typically, electronic device 124 may be connected to connections to other components in densitometer 100, or components outside densitometer 100 via electronic connectors 210b.

In some examples, receiver 134 is coupled to electronic device 126, as described above. Electronic device 126 may be coupled to other components of densitometer 100 via kinematic or quasi kinematic coupling as described above. Typically, electronic device 126 may have electronic connections to other components in densitometer 100, or components outside densitometer 100. Typically, electronic device 126 may be connected to connections to other components in densitometer 100, or components outside densitometer 100 via electronic connectors 210a.

As described above, spacer piece 140 is typically connected to side piece 116 and side piece 118, and, in some examples, other components of densitometer 100, via kinematic or quasi kinematic coupling.

As described above, electronic device 124 is typically connected to side piece 116 and, in some examples, other components of densitometer 100 via kinematic or quasi kinematic coupling.

As described above, electronic device 126 is typically connected to side piece 118 and, in some examples, other components of densitometer 100 via kinematic or quasi kinematic coupling.

Typically, the signal, typically light, from light source 132 travels through gap 110 and collimating lens 114, some of the light may be trapped in a reflection trap 123. Typically reflection trap 123 may be constructed from a black or dark material. In some examples, reflection trap 123 is configured to limit, and in some examples, prevent, reflections from collimating lens 114, focusing lens 112 and other reflections in densitometer 100 from reaching receiver 134.

As described above, in addition to the kinematic and, in some examples, quasi kinematic coupling within densitometer 100, and other couplings may also be used to connect components of densitometer 100. In some examples, these couplings may be accomplished by screws 141 or other methods of coupling.

In some examples, there may be one or a plurality of waterproofing connections 136, e.g., gaskets, o-rings, or other connectors, configured to waterproof densitometer 100, such that densitometer may be immersed fully or partially in a liquid, e.g., ink, as described above.

In some examples o-rings 175a or other similar devices are coupled to collimating lens 114 and to focusing lens 112. In some examples, collimating lens 114 and to focusing lens 112 may be shaped like rods, the shape configured to accept o-rings 175a or other similar devices.

Typically, the coupling of o-rings 175a or other similar devices to collimating lens 114 and/or to focusing lens 112 may be configured such that o-rings 175a or other similar devices seal the lens' radial surface. In some examples, the coupling of o-rings 175a or other similar devices to collimating lens 114 and/or to focusing lens 112 may be configured to prevent a fluid from entering and/or exiting gap 110 other than through inlet 106 and/or outlet 108, as described above.

Typically, the coupling of one or a plurality of o-rings 175a or other similar devices to collimating lens 114 and/or to focusing lens 112 may be configured such that o-rings 175a or other similar devices limit the effect of optical anomalies on densitometer 100. In some examples, the limitation of optical anomalies on densitometer 100 may include the limiting of optical reflections, wherein the optical reflections, may affect some accuracy of densitometer 100.

Typically, o-rings 175a or other similar devices may be coupled to the lenses such that o-rings 175 or other similar devices circumnavigate a circumference of focusing lens 112 and/or circumnavigate a circumference of collimating lenses 114.

Typically there may be o-rings 175b. O-rings 175b may be configured to be offset from a plane of symmetry running through lens 112 and 114, the offset of o-rings 175b configured to add downward force to maintain the position of collimating lens 114 and focusing lens 112 within densitometer 100. In some examples, o-rings 175b may be configured to offset a spring force resulting from steps 155 and 165, described below.

Typically, the reflections described above may originate in at least two areas: around gap 110 and in front of receiver 134, e.g., a photodiode or other sensor or detector, as described above. In some examples, reflections in the optical path may negatively influence the closed loop control of light source 132, as described above.

In some examples, light source 132 may have a closed loop sensor, the sensor configured to measure an output from light source 132. In some examples, the sensor may be a photodiode. In some examples the sensor may be configured to receive a portion of the output from light source 132, that portion diverted to the sensor by one or a plurality of beam splitters.

In some examples, densitometer may have an optical axis, the axis defined by the path of light through a set of optical components within densitometer 100, the optical components including light source 132, collimating lens 114, and focusing lens 112, and receiver 134. The optical axis may be defined as the straight line from light source 132 to the center of receiver 134. In some examples, the optical axis may be through the center of the polished spherical surface of the rod lenses, i.e., collimating lens 114, through the center of the polished base of collimating lens 114, through the gap, through the center of the polished base of focusing lens 112 through center of polished spherical surface of focusing lens 112 to the center of the receiver 134. In some examples the optical axis may also be the mechanical axis of the set of optical components.

In some examples, the polished spherical surface can be considered part of the circumference of an entire sphere, the center of the sphere lying on the optical axis.

In some examples, light source 132 may be tilted by 2 to 10 degrees, e.g., five degrees, off the optical axis, such that the polished base of collimating lens 114, the polished base described above, is configured to minimize the reflection of light back at the sensor in light source 132.

In some examples, collimating lens 114 may be tilted 2 to 10 degrees, e.g., 5 degrees, off the center of the sphere, described above, relative to the optical axis. The tilting of the collimating lens 114 does not alter the optical path, had collimating lens 114 not been tilted, as the polished spherical surface has not change off the optical axis of the set of optical components, such that the polished base of collimating lens 114, the polished base described above, is configured to minimize the reflection of light back at the sensor in light source 132.

In some examples, focusing lens 112 may be tilted 2 to 10 degrees, e.g., 5 degrees, off the center of the sphere, described above, relative to the optical axis. The tilting of the focusing lens 112 does not alter the optical path, had focusing lens 112 not been tilted, as the polished spherical surface has not change.

The tilting results in a translatory offset of the polished planar bases of collimating lens 114 and focusing lens 112. The tilting may further result in a minimization of reflections of light from within the gap, the reflections typically from the planar bases of collimating lens 114 and focusing lens 112. The tilting typically in the opposite direction of the tilting of collimating lens 114, such that light passing through focusing lens 112 does not reflect back at light source 132, the sensor in light source 132, or create other artifacts in densitometer 100.

In some examples, receiver 134 may be constructed from silicon, in some examples, the silicon may provide a reflection of light from light source 132. In some examples, receiver 134 may be configured to be tilted 2 to 10 degrees, e.g., 5 degrees, off the optical axis of the set of set of optical components, such that the reflection of light from receiver 134 does not become an artifact in a reading by densitometer 100.

The tilting of light source 132 and receiver 134 typically results in the light path from light source 132 traveling in an offset to the optical axis and not traveling symmetrically around the optical axis.

In some examples, the majority of the light path may travel above the optical axis.

In some examples light source 132, collimating lens 114, focusing lens 112 and receiver 134 are all tilted, typically to the same angle from the optical axis.

In some examples, when the light source 132, collimating lens 114, focusing lens 112 and receiver 134 are all tilted at the same angle, they can be regarded as parallel but offset.

In some examples, instead of tilting light source 132, collimating lens 114, focusing lens 112 and receiver 134, along the optical axis, the optical axis may be tilted and light source 132, collimating lens 114, focusing lens 112 and receiver 134 may be kept parallel, with an offset to each other.

Typically, light from light source 132 may be emitted from light source 132, and enter collimating lens 114 mostly above a mechanical axis of collimating lens. Light from light source 132 will typically be collimated by collimating lens 114, with a larger percentage of light from light source 132 traveling through collimating lens 114 above the mechanical axis of collimating lens 114. Light from light source 132 may be reflected off of the polished surface of collimating lens 114 and typically may reflect away from the sensor in light source 132.

Typically, light from light source 132 may continue to travel through gap 110 and through focusing lens 112. Light may be received by receiver 134. Some light may reflect off of a surface of receiver 134 and away from the sensor in light source 132. Some light reflected off of receiver 134 may be trapped in trap 123.

In some examples densitometer 100 may be configured such that collimating lens 114 and focusing lens 112 are offset.

In some examples, the optical path between light source 132 and receiver 134 through collimating lens 114, gap 110 and focusing lens 112 may not change when the optical components are tilted or offset from the optical axis. In some examples, the tilting and/or offsetting of the lenses may limit the effect of optical anomalies on densitometer 100. In some examples, the limitation of optical anomalies on densitometer 100 may include the limiting of optical reflections, wherein the optical reflections, may affect some accuracy of densitometer 100.

In some examples, by tilting and/or offsetting the lenses, the optical path of the light form light source 132 to receiver 134 may also be offset. Typically, when the optical path of the light form light source 132 to receiver 134 is tilted and/or offset reflections of light, typically light from light source 132, may be limited in at least two areas. Typically, the two areas where reflections of light from light source 132 may be limited, and in some examples, eliminated may include an area around gap 110 and an area in front of receiver 134.

In some examples, spacer piece 140 may be configured such that it positions one or a plurality of the optical components in densitometer 100, including collimating lens 114 and focusing lens 112 in an offset position, the position offset from the optical axis.

In some examples, spacer piece 140, typically milled from a single cylinder of aluminum, may provide dimensional stability to the densitometer 100 and to gap 110. In some examples, the dimensional stability may be provided due to the single piece nature of the center piece 140 and the configuration of spacer piece 140, the configuration such that gap 110 is maintained by non-moving pieces within spacer piece 140.

Typically with the lenses offset, spacer piece 140 may block those areas where the lens does not align. In some examples, by blocking the area where collimating lens 114 and focusing lens 112 do not align, spacer piece 140 may provide a step to which the lenses may abut. Typically step 155 abuts focusing lens 112 and step 165 abuts collimating lens 114.

In some examples, in providing steps 155 and 165 for the lens to abut, spacer piece 140 may be configured to prevent collimating lens 114 and focusing lens 112 from entering gap 110. In some examples, in providing a step to abut collimating lens 114 and focusing lens 112, spacer piece 140 may help maintain a width of gap 110, the width described above.

In some examples, steps 155 and 165 may also be configured to provide an area for a rinse channel. Typically rinse channels may include an upper rinse channel 232 and a lower rinse channel 230, as described above.

In some examples the off-axis or offset placement of collimating lens 114 and focusing lens 112 may prevent interference of the lens holder with the flow of fluids through gap 110.

In some examples the off-axis and/or offset placement of collimating lens 114 and focusing lens 112 may provide easy adjustment of the optical axes.

Figure 5:
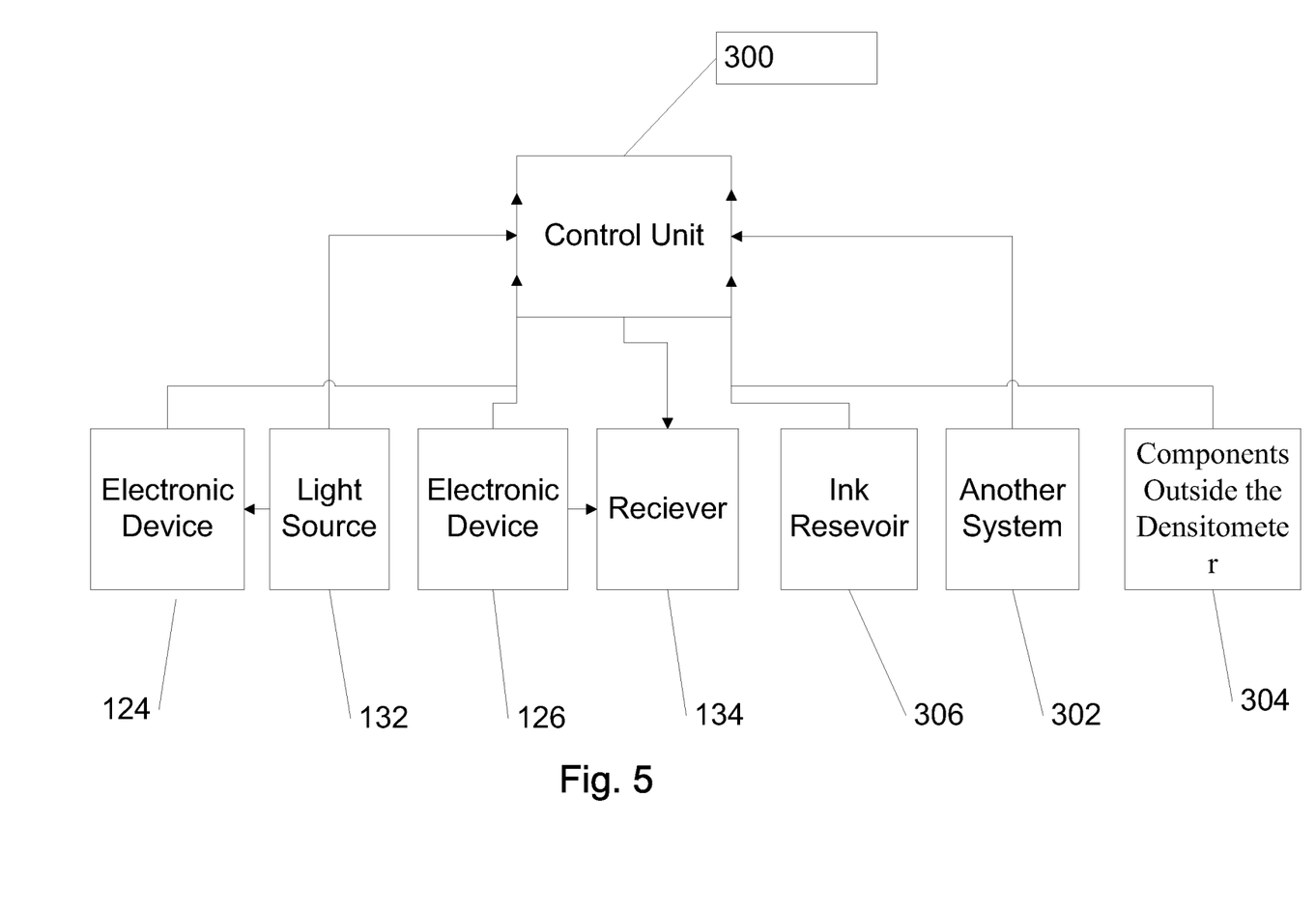

FIG. 5 is a schematic illustration of some of the interactions of a control unit 300. For example, a control unit 300 may be configured to determine, based on data regarding the traveling of light from light source 132 across gap 110, an experimental optical density of a fluid, the fluid passing from inlet 106 through gap 110 through outlet 108.

In some examples, control unit 300 may be configured to determine, based on data regarding the traveling of light from light source 132 across gap 110, an experimental optical density of ink, the ink passing from inlet 106 through gap 110 through outlet 108.

In some examples, control unit 300 may compare this experimental or observed optical density with a predicted optical density, and alter the fluid accordingly, as described below.

In some examples, control unit 300 may compare an experimental or observed optical density of an ink with a predicted optical density of the ink and alter the ink accordingly, as described below.

In some examples, control unit 300 may also control or be in contact with other components of densitometer 100, including electronic device 124. In some examples, control unit may be in contact with electronic device 126.

In some examples, control unit 300 may also control or be in contact with other components of densitometer 100, including light source 132 and receiver 134.

In some examples, control unit 300 may also control or be in contact with components outside the densitometer 304.

Control unit 300, in some examples, may control the flow of liquid from inlet 106 to outlet 108. In some examples, control unit 300 may control the flow of liquid via control over ink reservoir 306.

Control unit 300 may extract data from receiver 134 from a sampled duration, e.g., sample data from densitometer 100 over a number instances of fluid flowing through gap 110, or time, in order to increase the accuracy of measurements of the optical density of fluid.

In some examples, in response to the assessed optical density of fluid, as measured by densitometer 100, control unit 300 may signal another system 302 to alter the makeup of the fluid, such that the experimental optical density of the fluid is changed to reflect the expected optical density. In some examples, control unit may signal another system in a printer apparatus to alter the makeup of ink such that the experimental optical density of the ink is changed.

What is claimed is:

1. A densitometer for measuring an optical characteristic of a fluid, the densitometer comprising:
  a set of optical elements that include a light source, a collimating lens, a focusing lens, and a receiver, and
  an optical axis defined from the light source to a center of the receiver, said focusing and collimating lenses being located on the optical axis,
  wherein a gap exists between the collimating lens and the focusing lens so as to allow the fluid to pass in between the lenses, and
  wherein at least one of the optical elements is tilted with respect to an optical axis.

2. The densitometer of claim 1, wherein at least the collimating lens and the focusing lens are tilted with respect to the optical axis.

3. The densitometer of claim 1, wherein at least the light source and the receiver are tilted with respect to the optical axis.

4. The densitometer of claim 1, wherein the light source the receiver, the collimating lens and the focusing lens are tilted with respect to the optical axis.

5. The densitometer of claim 1, the densitometer further including a block, the block configured to align the collimating lens and the focusing lens in an offset position with respect to the optical axis.

6. The densitometer of claim 1, the densitometer further including one or a plurality of o-rings configured to maintain a position of at least one of the optical elements.

7. A densitometer comprising:
- a set of optical elements that include a light source, a plurality of lenses, and a receiver,
- a block configured to accept the plurality of lenses, each lens abutted against a one of a plurality of steps, wherein a gap exists between the plurality of lenses;
- an inlet and an outlet, the inlet and outlet configured to accept a flow of a liquid past the gap; and,
- a set of rinse channels defined by an area between one of the plurality of the steps and one of the plurality of the lenses, the rinse channels configured to direct some of the flow of the liquid, around the gap.

8. The densitometer of claim 7, wherein the rinse channels are configured to direct up to half the flow of a fluid around the gap.

9. The densitometer of claim 7, wherein a printed circuit board is configured to be coupled indirectly to the block via quasi-kinematic coupling.

10. The densitometer of claim 7, wherein the block is configured to have rotational symmetry.

11. The densitometer of claim 7, wherein the block is configured to provide dimensional stability to the densitometer.

12. A densitometer for measuring an optical characteristic of a fluid, the densitometer comprising:
- a set of optical elements that include a light source, a collimating lens, a focusing lens, and a receiver, the set of optical elements being parallel to each other, with an offset;
- wherein a gap exists between the collimating lens and the focusing lens so as to allow the fluid to pass in between the lenses; and,
- wherein an optical axis is tilted relative to a housing of the densitometer.

13. The densitometer of claim 1, further comprising an electronic device programmed to determine a percentage of solids in a fluid in the gap between the collimating lens and the focusing lens based on light from the light source received by the receiver.

14. The densitometer of claim 13, wherein the densitometer is watertight so as to be at least partially immersed in said fluid.

15. The densitometer of claim 13, wherein the light source is configured to produce an optical signal according to a wave function.

16. The densitometer of claim 13, further comprising a kinematic coupling between the electronic device and at least one of a light source holder holding the light source and a receiver holder holding the receiver.

17. The densitometer of claim 1, further comprising an outlet for fluid to leave the gap between the collimating and focusing lenses, said outlet being connected to a printer head.

18. The densitometer of claim 1, further comprising rinse channels communicating with the gap between the collimating and focusing lenses for providing a rinsing solution to rinse the gap.

19. The densitometer of claim 1, further comprising an anti-reflective coating on a base of the focusing or collimating lens.

20. The densitometer of claim 1, wherein the focusing and collimating lenses are rod lenses.

* * * * *